United States Patent [19]

Hansen, Jr. et al.

[11] Patent Number: 4,758,675
[45] Date of Patent: Jul. 19, 1988

[54] 3-THIOPHENE-SUBSTITUTED TYROSYL DIPEPTIDE AMIDES

[75] Inventors: Donald W. Hansen, Jr., Chicago; Barnett S. Pitzele, Skokie; Robert W. Hamilton, Wilmette; Michael Clare, Skokie, all of Ill.

[73] Assignee: G. D. Searle & Co., Chicago, Ill.

[21] Appl. No.: 14,339

[22] Filed: Feb. 13, 1987

Related U.S. Application Data

[63] Continuation-in-part of Ser. No. 882,794, Jul. 14, 1986, which is a continuation-in-part of Ser. No. 829,266, Feb. 14, 1986, abandoned, which is a continuation-in-part of Ser. No. 765,882, Aug. 14, 1985, abandoned.

[51] Int. Cl.$^4$ ............................................. C07D 333/22
[52] U.S. Cl. ................................................... 549/77
[58] Field of Search ............................ 260/998.2; 549/77

[56] References Cited

U.S. PATENT DOCUMENTS

| | | |
|---|---|---|
| 4,127,535 | 11/1978 | Coy et al. . |
| 4,261,888 | 4/1981 | Bauer et al. . |
| 4,273,704 | 6/1981 | Mazur . |
| 4,316,892 | 2/1982 | Jones . |
| 4,405,607 | 9/1983 | Cardinaux et al. . |
| 4,407,746 | 10/1983 | Mazur et al. . |
| 4,450,155 | 5/1984 | Morgan ........................ 260/998.2 |
| 4,454,120 | 6/1984 | Morgan ........................ 260/998.2 |
| 4,533,655 | 8/1985 | Morgan ........................ 260/998.2 |
| 4,533,657 | 8/1985 | Morgan ........................ 260/998.2 |
| 4,599,325 | 7/1986 | Hansen et al. . |

OTHER PUBLICATIONS

Kiso et al., Synthesis and Activity of Short Chain Enkephalin-Like Peptides Peptide Chemistry 1981, T. Shiori (Ed), Protein Res. Foundation, Osaka (1982).
Vavarek et al., Peptides, 2, pp. 303–308 (1981).

*Primary Examiner*—Alan Siegel
*Attorney, Agent, or Firm*—Frank P. Grassler; Paul D. Matukaitis

[57] ABSTRACT

This invention relates to novel 3-thiophene-substituted tryosyl dipeptide amides of the formula:

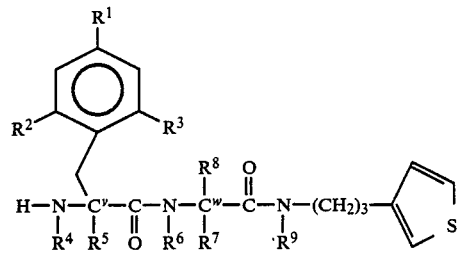

and the pharmaceutically acceptable addition salts thereof, wherein $R^1$ is —OH, benzyloxy, or —OCH$_3$; wherein $R_2$ and $R_3$ may be the same or different and represent lower alkyl of 1–6 carbon atoms; wherein $R^4$, $R^5$, $R^6$, $R^7$, $R^8$, and $R^9$ may be the same or different and represent hydrogen or lower alkyl of 1–6 carbon atoms; wherein "v" represents an asymmetric carbon atom that may be racemic or that may have the D or L configuration; and wherein "w" represents an asymmetric carbon atom that has the D configuration. These compounds are useful as analgesic agents.

4 Claims, No Drawings

3-THIOPHENE-SUBSTITUTED TYROSYL DIPEPTIDE AMIDES

This application is a continuation-in-part of pending Ser. No. 882,794 filed July 14, 1986, which is a continuation-in-part of Ser. No. 829,266, filed Feb. 14, 1986, now abandoned, which is a continuation-in-part of Ser. No. 765,882, filed Aug. 14, 1985, also now abandoned.

FIELD OF THE INVENTION

The present invention relates to novel 3-thiophene substituted tyrosyl dipeptide amides. In particular, it provides novel derivatives of Formula I which are useful as analgesic agents.

BACKGROUND OF THE INVENTION

In 1975, a pentapeptide, methionine enkephalin, was reported by Hughes et al., *Nature*, 258, 577 (1975). This peptide is found in many areas of the brain where it appears to act as a neurotransmitter or neuromodulator in a central painsuppressant system. This naturally occurring peptide binds stereospecifically to partially purified brain opiate receptor sites. See for example, Bradberry et al., *Nature*, 260, 793 (1976). It is also highly active in bioassays for opiate activity but exhibits only weak, fleeting analgesic activity when injected directly into the brain of the rat, see for example, Belluzi et al, *Nature*, 260, 625 (1976).

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example, methyl or halo, modifying the C-terminus, etc., to produce enkephalin derivatives of varying properties and potencies.

Kiso, et al., *Peptide Chemistry* 1981,: 65–70, Protein Research Foundation, Osaka, Japan (1982), disclosed the synthesis and activity of short chain enkephalin-like peptides, among them tripeptide and dipeptide alkylamides such as N-methyltyrosine-(D)-methionine sulfoxide-glycine-methylphenethylamide and tyrosine-(D)-methionine sulfoxide-phenylpropylamide.

Vavrek, et al., *Peptides* 2, 303, 1981 disclosed analogs of enkephalin, among them the dipeptide tyrosine-D-alanine phenylpropylamide, (Tyr-(D)Ala-PPA).

Hansen, et al., U.S. Pat. No. 4,599,325, which issued July 8, 1986 to the inventors of the present invention, discloses tyrosyl dipeptide amides possessing analgesic activity in mammals.

When compared to the Vavrek, et al. compound, the compounds of this invention have unexpected and surprisingly superior properties. The present invention provides new dipeptide derivatives which show improved potency as analgesic agents by both oral and parenteral routes of administration. Additionally, U.S. Pat. No. 4,316,892 relates to certain methionine enkephalin derivatives useful as analgesic agents.

SUMMARY OF THE INVENTION

This invention encompasses analgesic tyrosine derivatives of formula I:

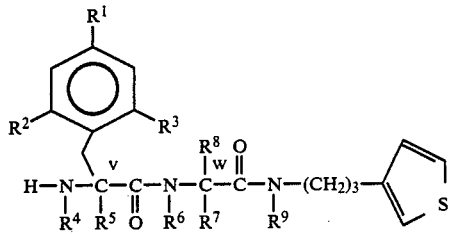

and the pharmaceutically acceptable addition salts thereof wherein $R^1$ is —OH, OCH$_3$, or contemplated equivalents including lower alkoxy and benzyloxy; wherein $R^2$ and $R^3$ may be the same or different and represent straight or branched chain lower alkyl of 1–6 carbon atoms; wherein $R^4$, $R^5$, $R^6$, $R^7$, $R^8$, and $R^9$ may be the same or different and represent hydrogren or straight or branched chain lower alkyl of 1–6 carbon atoms; wherein "v" represents an asymmetric carbon atom that may be racemic or that may have the D or L configuration; and wherein "w" represents an asymmetric carbon atom that has the D configuration.

DETAILED DESCRIPTION

The compounds described in this invention are prepared according to the reaction sequence outlined in Scheme I. In Scheme I, a D-amino acid derivative (X), having its amino group blocked by "Z", is transformed into a mixed anhydride by reaction with isobutylchloroformate (IBCF) in the presence of N-methyl-morpholine (NMM). the mixed anhydride is then coupled to the amino group of 3-(3-thienyl)-1-propamine to form an amide linkage. The amino blocking group, t-butoxycarbonyl, (Boc), is then removed by hydrolysis in 6N HCl/dioxane to provide the D-amino amide (XII). Similarly, a 2,6-dialkyl amino-blocked-D,L-tyrosine derivative (XIII) is transformed into a mixed anhydride by reaction with isobutylchloroformate and N-methylmorpholine. The resulting mixed anhydride is then coupled with the amino group on the D-amino amide (XII) to produce a 3-thiophene substituted tyrosyl dipeptide amide as a mixture of diastereomers (XIV).

The resulting pair of diastereomers can be separated by methods well known in the art, such as by chromatography, crystalization and the like, to produce the individual stereoisomers. The individual stereoisomers can then be deblocked by hydrolysis with 6N HCl/dioxane to produce the compounds of Formula I.

In Scheme I, "Boc" refers to the amino blocking group t-butoxy carbonyl; $R^1$ through $R^9$ are as previously defined. The "Z" of compound X represents the amino blocking group "Boc" or benzyloxycarbonyl. In sulfur containing X, the Z is preferably Boc and it can be removed by hydrolysis with 6N HCl/dioxane. The thiophene utilized in the present invention does not qualify as a sulfur containing X, since the sulfur is part of an aromatic system and is not free to react.

Analagous to the enhanced analgesic properties of tyrosyl dipeptides already disclosed in our co-pending applications, (Ser. No. 882,794, filed July 14, 1986; Ser. No. 829,266, filed. Feb. 14, 1966; and Ser. No. 765,882 filed Aug. 14, 1985) the dipeptide compounds of the present invention possess unexpectedly superior analgesic activity over the enkephlin-like dipeptides disclosed by Vavrek. More specifically, Ser. No. 882,794 disclosed tyrosyl dipeptide amides of the formula:

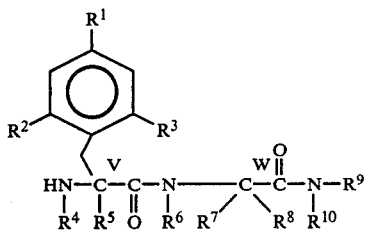

and the pharmaceutically acceptable acid addition salts thereof wherein $R^1$ is hydrogen, lower alkyl, hydroxy, $-OCO_2$ lower alkyl, lower alkoxy, $-O(CH_2)_n$-phenyl with the phenyl optionally substituted by halogen, $-NO_2$, $-CN$, $-NH_2$ or lower alkyl wherein n is 1 to 4; $R^2$ and $R^3$ represent lower alkyl, halogen, or lower alkoxy, or either one or $R^2$ or $R^3$ is hydrogen and the other is lower alkyl, lower alkoxy or halogen; $R^4$, $R^5$, $R^6$, $R^7$, $R^8$, and $R^9$ may be the same or different and represent hydrogen or lower alkyl; $R^{10}$ is selected from the group consisting of

—(ALK)X where ALK represent alkylene, thioalkylene, oxyalkylene, having 1 to 5 carbon atoms; alkenylene and alkynylene having 2 to 4 carbon atoms; and X represent pyridyl, pyrimidinyl, 9H-fluoren-9-yl, diphenylmethyl, thienyl, carboxy, lower alkoxy carbonyl, substituted phenyl wherein the phenyl substituent is amino, hydroxy, halogen, nitro, methylenedioxy, lower alkyl, carboxy, lower alkoxycarbonyl, lower alkoxy, carboxamide, diloweralkylamino or X represents phenyl when ALK is not alkylene; or $R^{10}$ is

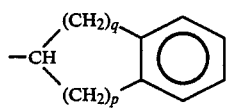

where p and q are independently 1 to 4; or $R^9$ and $R^{10}$ together with N is

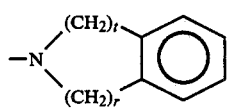

where r and t are independently 1 to 4; v represents an asymmetric carbon that may be racemic or have the D or L configuration; w represents an asymmetric carbon when $R^7$ and $R^8$ are not the same that maybe racemic or have the D or L configuration. These compounds are useful as analgesic and/or antihypertensive compounds.

SCHEME I

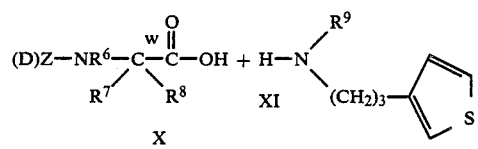

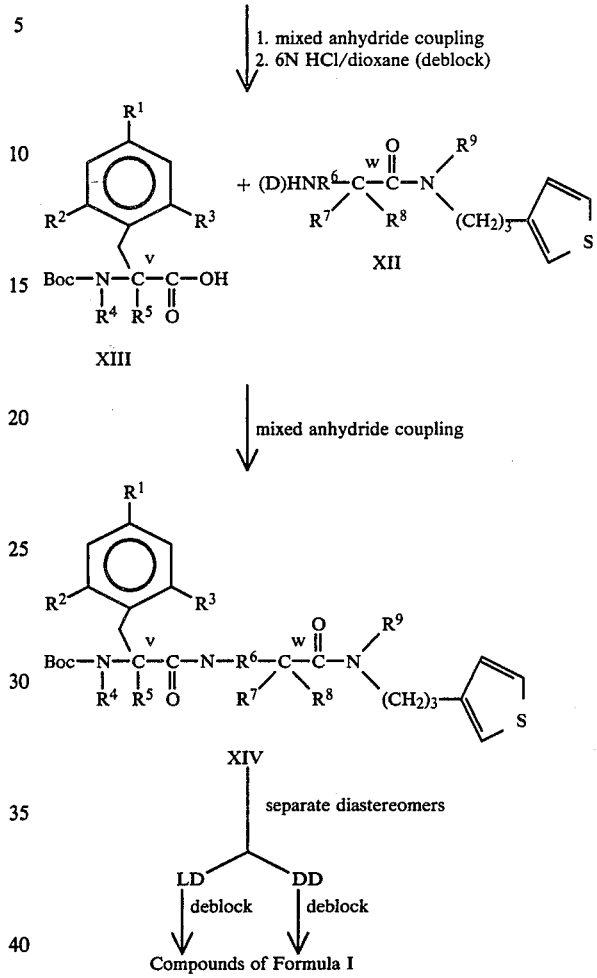

The analgesic activity for the compounds of the present invention is illustrated by their respective activities in the Writhing and Opiate Binding Assays. In some cases, the analgesic activity of the representative compounds was compared with that of a disclosed analog of enkephalin, (L)-tyrosine-(D)-alaninylphenylpropylamide.

Writhing Assay

Male Charles River albino mice (CD-1/HAM/1LR) weighing between 20 and 30 grams were used. Thirty minutes after subcutaneous or intragastric administration of a dose (0.1 mg/10 gram body weight), of the test compound, a 0.025% (w/v) phenylbenzoquinone solution was injected intraperitoneally (0.1 ml/10 gram body weight). Five minutes later, each mouse was placed in a large glass beaker and the number of writhes that occurred in the subsequent ten minutes was counted. A writhe consisted of dorsoflexion of the back, extension of the hindlimbs, and strong contraction of the abdominal musculature. The test compound was considered to have produced analgesia in a mouse if the number of writhes elicited by phenylbenzoquinone was equal to or less than one-half the median number of writhes recorded for the saline-treated group that day. The results were expressed as the number of mice (out of a possible ten) in which the test compound produced analgesia. The test compound was rated active if the number of writhes in the drug treatment group was significantly less than the number of writhes in the saline treatment group as determined by a one-way analysis of variance. If the initial test dose of 10 mg/kg inhibited writhing in greater than 6 of 10 mice, the effect of additional doses was evaluated and an $ED_{50}$ value was calculated using a maximum likelihood function.

Opiate Binding Assay

The test compounds were evaluated for their ability to displace the binding of $^3$H-Naloxone to opiate receptors isolated from rat brain. Male rats [Crl: CD(SD) BR] obtained from Charles River Laboratories (Portage, Mich.) were sacrificed by cervical dislocation. A purified homogenate of receptor membranes was prepared from the brains according to the method described by Chang and Cuatrecasas. (K.-J. Chang and P. Cuatrecasas. Multiple Opiate Receptors: Enkephalins and Morphine Bind to Receptors of Different Specificity. *J. Biol. Chem.* 254, 2610–2618 (1979).) The brains were homogenized in 10 volumes of 0.32M sucrose and centrifuged twice at 6,00xg for 15 minutes. Following centrifugation of the supernatants at 40,000xg for 30 minutes, the pellets were resuspended in 5 mM tris HCl, and centrifuged at 6,000. The supernatant was centrifuged at 40,000xg. The resuspension in 5 mM tris and centrifugation was repeated twice. The final pellet was resuspended in 2 volumes of 50 mM tris HCl (pH 7.4). The homogenate was assayed for protein content according to the method of Itzhaki and Gill (R. F. Itzhaki and D. M. Gill. A Micro-Biuret Method for Estimating Proteins. *Anal. Biochem.* 9, 401–410 (1964).)

The binding of the test compounds to the receptor membrane preparation was measured using a modification of the method of Pert and Snyder (C. B. Pert and S. H. Snyder. Properties of Opiate-Receptor Biding in Rat Brain. *Proc. Natl. Acad. Sci.* 70, 2243–2247 (1973)). The receptor assay was run using a final concentration of 1 nM $^3$H-Naloxone and 0.5 mg/ml of homogenate protein. Levorphanol ($1\times 10^{-5}$ M) was used as the displacer for non-specific binding. The final concentration of the test compounds was $10^{-5}$ M. The assay was run 0.05 M tris HCl (pH 7.4). Total assay volume was 1.0 ml.

Samples were incubated at 25° C. for 60 min., filtered over Whatman GF/C glass fiber filters and rinsed twice with 2.4 ml washes of ice-cold buffer. The filters were air dried at 50° C. for 30 min. After drying, 10 ml. of PCS was added to the vial and radioactivity determined using a Tracor Analytic Mark III liquid scintillation counter with a counting effiency of 48%.

The $IC_{50}$ values, the concentration of the test compounds which inhibited $^3$H-Naloxone specific binding to the opiate receptor by 50%, were obtained from log-logit plots of concentration-response curves.

The compounds of the present invention, as represented by Formula I, can be administered in such oral dosage forms as tablets, capsules, pills, powders, granules, suspensions, or solutions. They may also be administered rectally or vaginally, in such forms as suppositories or bougies. They may also be introduced in the form of eyedrops, or they may be administered intraperitoneally, subcutaneously, or intramuscularly, using forms known to the pharmaceutical art. In general, the preferred route of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, and the route of administration of the particular compound employed. An ordinary skilled physician or veterinarian will readily determine and prescribe the therapeutically effective dosage based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula I can also be administered as pharmaceutically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula I is generally not of critical importance, being chosen principally for convenience or for maximum yields. Moreover, the choice of activating reagents and conditions for joining amino acids or small peptides is not limited to those specifically described herein. The peptide intermediates and products of this invention are typically purified by crystallization or by column chromatography. Furthermore, where racemic amino acid starting materials are employed, the intermediates and products may be separated by column chromatography into their individual diastereomers.

The accompanying examples illustrate the methods used to prepare the compounds of this invention. These examples are given by way of illustration only and in no way should be construed as limiting the invention in spirit or in scope, as many modifications in materials and methods will be apparent from this disclosure to those skilled in the art.

DESCRIPTION OF THE PREFERRED EMBODIMENT

EXAMPLE 1

.1,1-dimethylethyl[1R-methyl-2-oxo-2-[[3-(3-thienyl)-propyl]amino]ethyl]cabonate

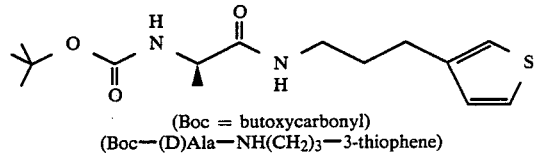

(Boc = butoxycarbonyl)
(Boc—(D)Ala—NH(CH$_2$)$_3$—3-thiophene)

To 5.1 g (26.9 mmol) of Boc-(D)-Alanine in 100 ml of CH$_2$Cl$_2$ at 0° C. was added with vigorous stirring 5.9 ml (53.8 mmol) of N-methylmorpholine (NMM). After cooling this vigorously stirred solution to −78° C., 3.5 ml (26.9 mmol) of isobutylchloroformate (IBCF) were added to this reaction which was run entirely under an argon atmosphere. The mixture was allowed to warm slowly to 20° C. before it was again cooled to −78° C. and 3.8g (26.9 mmol) of 3-(3-thienyl)-1-propanamine were added in a single portion. Following warming this mixture to room temperature, it was allowed to stir 25 additional hours. Precipitated N-methylmorpholine hydrochloride was filtered off and the filtrate was diluted with CH₂Cl₂ (200 ml) and washed 3× with 100 ml of 0.5N potassium bisulfate (KHSO₄). The combined aqueous washes were extracted with a 100 ml portion of CH₂Cl₂ and the combined organics were washed 1× with 75 ml of brine, dried (Na₂SO₄), and stripped of all solvent under reduced pressure. The residue was essentially one spot on thin layer chromatography when eluted with 10% ethanol in chloroform. The material was used in subsequent reactions without further purification.

Optical rotation $[\alpha]_D + 31.3°; +87.8°$ (365 nm) CHCl₃.

Analysis for C₁₅H₂₄N₂O₃S (MW=312.43): Calcd: C, 55.36; H, 8.98; N, 8.61. Found: C, 55.82; H, 8.50; N, 8.12.

EXAMPLE 2

2R-amino-N-[3-(3-thienyl)propyl]propanamide

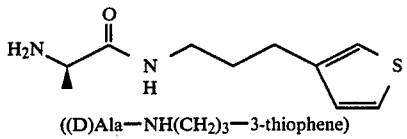

((D)Ala—NH(CH₂)₃—3-thiophene)

The product of Example 1 was dissolved in 100 ml of acetic acid. To this solution was added a 10 fold millimolar excess of 6.0N HCl/dioxane. This solution was then gently stirred under a nitrogen atmosphere at room temperature for one hour before all solvent was removed under reduced pressure. The resulting oil residue was washed liberally with diethyl ether before being dried under vacuum to yield the titled product. This material was used in subsequent experiments without further purification.

Optical rotation $[\alpha]_D - 5.1°; -85.1°$ (365 nm) CHCl₃.

Analysis for C₁₀H₁₆N₂OS.1/4H₂O (MW=216.81): Calcd: C, 55.40; H, 7.67; N, 12.92; S, 14.78. Found: C, 55.62; H, 7.46; N, 12.98; S, 14.66.

EXAMPLE 3

N-[(1,1-dimethylethoxy)carbonyl]-2,6-dimethyl-DL-tyrosyl-N-[3-(3-thienyl)propyl]-D-alaninamide

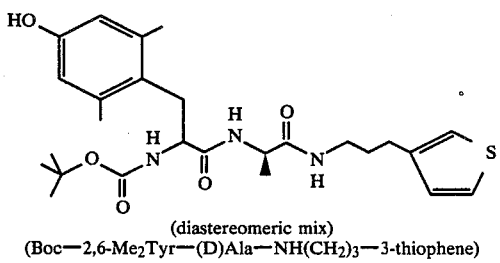

(diastereomeric mix)
(Boc—2,6-Me₂Tyr—(D)Ala—NH(CH₂)₃—3-thiophene)

Racemic t-butoxycarbonyl-2,6-dimethyltyrosine (3.5g, 11.3 mmol) in 40 ml of CH₂Cl₂ was stirred with molecular sieve 5A under argon for 30 min. before being cooled to 0° C. NMM (1.24 ml, 11.3 mmol) was added to this mixture before it was cooled further to −78° C. IBCF (1.5 ml, 11.3 mmol) was then added and the mixture was allowed to warm to room temperature. After 30 min. at room temperature, the reaction was cooled to −78° C. and charged with 2.4 g (11.3 mmol) of the title compound of Example 2. This mixture wsa allowed to warm to room temperature and stir an additional 18 hrs. The crude product mixture of diastereomers, obtained on workup as described in Example 1, was separated by preparatory liquid chromatography (PLC) on Woelm® silica eluting with 1.5% MeOH/CHCl₃.

Diastereomer DF $[\alpha]_D - 12.7°; +4.5°$ (365nm)CHCl₃.

N.M.R. shift of the (D)Ala methyl=1.20 δ(DMSO-d₆).

Analysis for C₂₆H₃₇N₃O₅S (MW=503.67): Calcd: C, 62.00; H, 7.40; N, 8.34; S, 6.36. Found: C, 62.41; H, 7.62; N, 8.13; S, 6.37.

Diastereomer UF $[\alpha]_D + 34.5°; +144.5°$ (365 nm) CHCl₃.

N.M.R. shift of the (D)Ala methyl=1.05 δ(CD₂Cl₂).

Analysis for C₂₆H₃₇N₃O₅S.1/4H₂O (MW=508.16): Calcd: C, 61,45; H, 7.44; N, 827; S, 6.31. Found: C, 61.53; H, 7.56; N, 8.10; S, 7.01.

EXAMPLE 4

2,6-dimethyltyrosyl-N-[3-(3-thienyl)propyl]-D-alaninamide, monohydrochloride

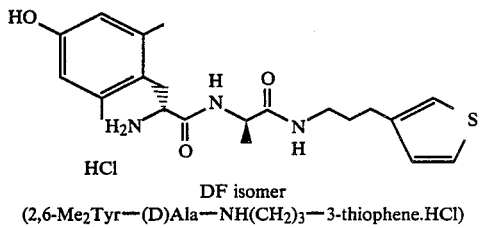

DF isomer
(2,6-Me₂Tyr—(D)Ala—NH(CH₂)₃—3-thiophene.HCl)

The DF diastereomer of Example 3 was dissolved in 25 ml of acetic acid. To this stirred solution at room temperature under nitrogen was gently added 6 ml of 6N HCl/dioxane. After 1 hr., all of the solvent was removed under room temperature. The resulting oil was shaken with diethyl ether to produce the solid salt. The salt was suction filtered, washed with diethyl ether and dried under vacuum.

Optical rotation $[\alpha]_D - 59.6°; -223.0°$ (365 nm)CH₃OH.

N.M.R. shift of the (D)Ala methyl=1.20 δ(CD₃OD).

Analysis for C₂₁H₃₀N₃O₃SCl (MW=440.00): Calcd: C, 57.33; H, 6.87; N, 9.55; S, 7.29; Cl, 8.06. Found: C, 57.29; H, 7.08; N, 9.78; S, 7.47; Cl, 7.82.

EXAMPLE 5

2,6-dimethyltyrosyl-N-[3-(3-thienyl)propyl]-D-alaninamide, monohydrochloride

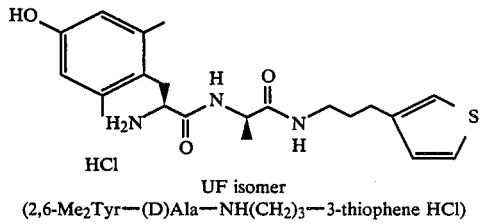

UF isomer
(2,6-Me₂Tyr—(D)Ala—NH(CH₂)₃—3-thiophene HCl)

The titled product was prepared by the method of Example 4 substituting the UF isomer of Example 3 for the DF isomer.

Optical rotation $[\alpha]_D + 27.5°; +393.3°$ (365 nm)CH₃OH.

N.M.R. shift for the (D) Ala methyl=1.04 (CD₃OD).

Analysis for $C_{21}H_{30}N_3O_3SCl$ (MW=440.00): Calcd: C, 57.33; H, 6.87; N, 9.55; S, 7.29; Cl, 8.06 Found: C, 56.98; H, 7.00; N, 9.64; S, 7.41; Cl, 7.26.

What is claimed is:

1. A compound of the formula:

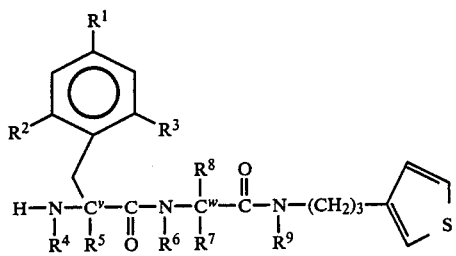

and the pharmaceutically acceptable addition salts thereof, wherein $R^1$ is —OH, benzyloxy or —OCH$_3$; wherein $R^2$ and $R^3$ may be the same or different and represent straight or branched chain lower alkyl of 1–6 carbon atoms; wherein $R^4$, $R^5$, $R^6$, $R^7$, $R^8$, and $R^9$ may be the same or different and represent hydrogen or straight or branched chain lower alkyl of 1–6 carbon atoms; wherein "v" represents an asymmetric carbon atom that may be racemic or that may have the D or L configuration; and wherein "w" represents an asymmetric carbon atom that has the D configuration.

2. A compound according to claim 1 of the formula:

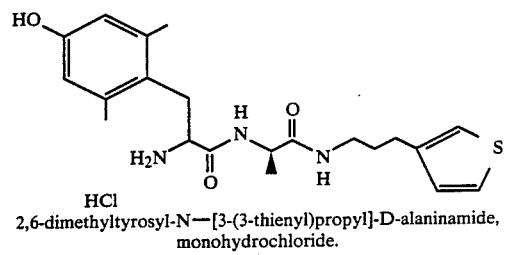

2,6-dimethyltyrosyl-N—[3-(3-thienyl)propyl]-D-alaninamide, monohydrochloride.

3. A compound according to claim 1 of the formula:

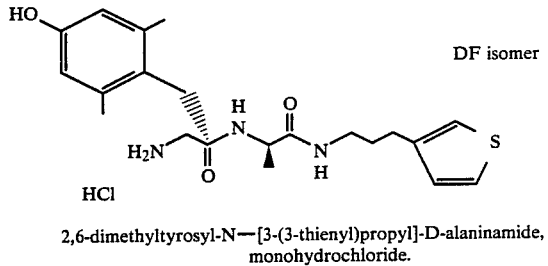

DF isomer 2,6-dimethyltyrosyl-N—[3-(3-thienyl)propyl]-D-alaninamide, monohydrochloride.

4. A compound according to claim 1 of the formula:

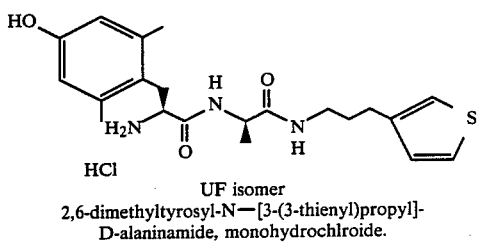

UF isomer
2,6-dimethyltyrosyl-N—[3-(3-thienyl)propyl]-D-alaninamide, monohydrochlroide.

* * * * *

UNITED STATES PATENT AND TRADEMARK OFFICE
CERTIFICATE OF CORRECTION

PATENT NO. : 4,758,675
DATED     : July 19, 1988
INVENTOR(S) : Hansen, Jr., et al.

It is certified that error appears in the above-identified patent and that said Letters Patent is hereby corrected as shown below:

Column 1, line 15, reading "novel derivatives" should read -- novel dipeptide derivatives --.

Column 5, line 22, reading "6,00xg" should read -- 6,000 xg --.

Column 10, the second structure, that portion of the structure reading

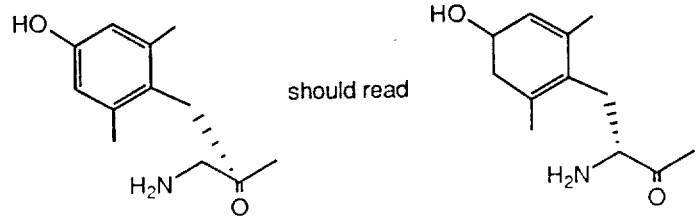

Signed and Sealed this

Twenty-seventh Day of March, 1990

Attest:

JEFFREY M. SAMUELS

*Attesting Officer*     *Acting Commissioner of Patents and Trademarks*